United States Patent

Weaver

[19]

[11] Patent Number: 4,722,786

[45] Date of Patent: Feb. 2, 1988

[54] HEAD FOR A PREPARATIVE COLUMN

[76] Inventor: Victor C. Weaver, The Brambles, Well St., Loose Village, Maidstone, Kent, United Kingdom, ME15 0EW

[21] Appl. No.: 28,051

[22] PCT Filed: May 13, 1985

[86] PCT No.: PCT/EP85/00228

§ 371 Date: Dec. 31, 1985

§ 102(e) Date: Dec. 31, 1985

[87] PCT Pub. No.: WO85/05285

PCT Pub. Date: Dec. 5, 1985

Related U.S. Application Data

[63] Continuation of Ser. No. 822,407, Dec. 31, 1985, abandoned.

[30] Foreign Application Priority Data

May 23, 1984 [GB] United Kingdom ............ 8413121

[51] Int. Cl.⁴ .............................................. B01D 15/08
[52] U.S. Cl. .................................. 210/198.2; 55/386; 422/70; 422/211; 422/310
[58] Field of Search ...................... 422/70, 211, 310; 210/198.2; 55/386; 436/161

[56] References Cited

U.S. PATENT DOCUMENTS

| | | | |
|---|---|---|---|
| 3,298,527 | 1/1967 | Wright | 210/198.2 |
| 3,511,377 | 5/1970 | Hrdina | 210/198.2 |
| 3,780,866 | 12/1973 | Ek | 210/198.2 |

FOREIGN PATENT DOCUMENTS

| | | | |
|---|---|---|---|
| 0106419 | 4/1984 | European Pat. Off. | 210/198.2 |
| 1190282 | 4/1970 | United Kingdom | 422/310 |

*Primary Examiner*—Ernest G. Therkorn
*Attorney, Agent, or Firm*—Burns, Doane, Swecker & Mathis

[57] ABSTRACT

A head for uniformly dispersing a liquid over the input surface of a chromatographic or reactive bed in a preparative column having a predetermined back pressure per unit flow rate, comprising an inlet tube through which the liquid is supplied. According to the invention the inside of the head (1) is profiled so that the vertical liquid flow through the bed is equated to the horizontal liquid flow in the head with due consideration to said back pressure of the column.

6 Claims, 4 Drawing Figures

HEAD FOR A PREPARATIVE COLUMN

This application is a continuation, of application Ser. No. 822,407, filed Dec. 31, 1985, now abandoned.

TECHNICAL FIELD

The invention relates to a head for uniformly dispersing a liquid over the input surface of a chromatographic or reactive bed in a preparative column having a predetermined back pressure per unit flow rate, comprising an inlet tube through which the liquid is supplied.

BACKGROUND ART

For a chromatographic separation it is common to utilize at least three diffrent liquids, namely a sample liquid, a wash liquid, and an elution liquid.

These liquids are transferred to the chromatographic column by means of a pump, and each liquid is selected in turn by a tap or rotary valve.

The liquids will be pumped through conveniently sized tubing to the chromatographic column which may be 10 or 100 times larger in diameter than the tubing.

It is necessary that the connecting tubing is relatively small in diameter so that the liquids are delivered in a plug-flow manner. Thereby, the liquids will not experience excessive drag at the wall of the tubing or diffusion with the liquids in front and behind, respectively.

In known columns the liquids enter the distribution region of the columns in a turbulent state with a linear velocity which is normally 300–1000 times higher than the linear flow velocity through the column.

This sudden change in velocity tends to induce mixing of the liquids, and makes the sample trail onto a column during the sample loading stage.

DISCLOSURE OF INVENTION

The object of the invention is to bring about a distribution head for a preparative column, which effectively reduces the input velocity of the pumped liquids, and creates a uniform laminar flow over the input surface of the bed in the column.

This is attained in that the head according to the invention has obtained the characterizing features defined in the claims.

BRIEF DESCRIPTION OF DRAWINGS

The invention will be described more in detail below with reference to the drawings on which

DETAILED DESCRIPTION

Figure 1:
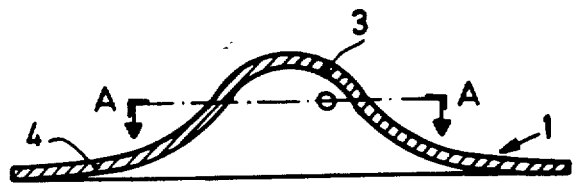
FIG. 1 is a cross-sectional view of one embodiment of a head according to the invention.
Figure 2:
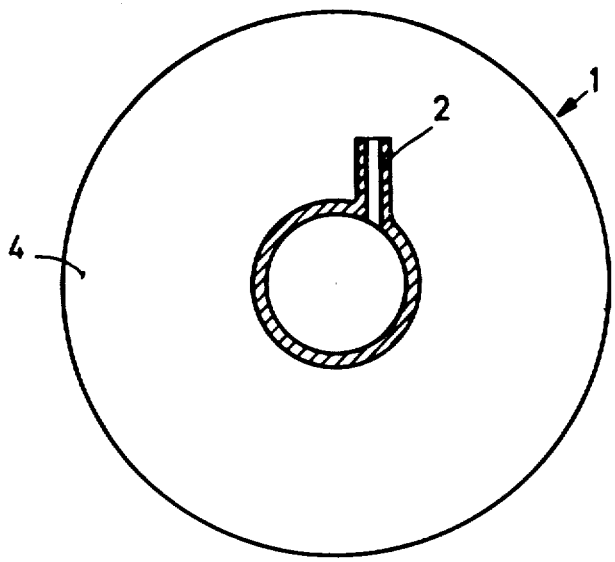
FIG. 2 is a sectional view along line A—A in FIG. 1.

FIGS. 1 and 2 show a first embodiment of a head according to the invention for uniformly dispersing a liquid over the input surface of a chromatographic or reactive bed in a preparative column (not shown). The head is denoted 1 and comprises an inlet tube 2 through which the liquid is supplied.

To uniformly disperse a liquid onto such a bed (not shown) it is necessary for the head 1 to induce laminar flow of the liquid. The head 1 should, therefore, effectively reduce the input velocity of the pumped liquids and create a uniform laminar flow over the input surface of the bed in the column (not shown), and this should be accomplished in the minimum volume to limit diffusion between contiguous quantities of liquid entering the head 1.

Thus, the liquid flow through the packed column bed should be equated to horizontal liquid flow in the head 1, which means that liquid for the outer bed region must be supplied by liquid flowing from the centre of the head 1.

According to the invention the head 1 has a central domed part 3 into which the inlet tube 2 enters. The central domed part blends into a profiled lower part 4, the profile of which is described by the equation $$h_x = \frac{1}{z}\left(\frac{R^2 - x^2}{x}\right)$$

where
R is the internal radius of the column (not shown),
$h_x$ is the vertical distance between the base of the head 1 and the inside surface of the profiled part 4 at a distance x from the central vertical axis of the head 1, and
z is a constant proportional to the predetermined back pressure of the column. x is smaller than or equal to R, and greater than or equal to R/15, preferably greater than or equal to R/4.

The object of the central domed part 3 which may be e.g. semi-spherical or of an arched vertical cross-sectional form, is to destroy the excess kinetic energy of the input liquid, and to form a laminar flow region prior to the liquid entering into the wider profiled part 4.

To enforce the loss of kinetic energy the inlet tube 2 is horizontal and enters into the domed part 3 at a point between a line through the central vertical axis of the head 1 and a line tangential to the inside surface of the domed part 3.

If there was no back pressure to the liquid flow within the column, i.e. the column is not filled with a packed bed, z would be equal to 2, but since the liquid flow from within the head 1 is severely restricted by the relatively high back pressure of the column, z is dependent on that back pressure. For a typical aqueous solution and back pressures of e.g. 0.4, 1.0, and 3.0 bar, z would be about 9, 15 and 25, respectively.

For columns of an internal radius 250 mm it may be advantageous to incorporate a central distributing body 5 (FIG. 3) in the space between the base of the head 1 and the domed part 3 to aid the uniform distribution. The distributing body is attached to the head 1 by means of e.g. three or four arms 6. The diameter of the body 5 is preferably about the same as the diameter of the domed part 3.

By means of the distributing body 5 it is possible to minimize the liquid volume present in the head, and hence minimize diffusional processes, and to stabilize laminar flow of the liquid as it moves towards the column bed.

The top side of the distributing body 5 tapers upwardly and forms a point directed towards the top of the domed part 3. The top taper preferably runs parallel to the profile of the profiled part 4. The bottom side of the distributing body 5 extends essentially down to the base of the head 1, and is profiled in accord with the principles described by the above equation defining $h_x$.

By means of the head 1 according to the invention it is possible to reduce a turbulent liquid inlet velocity to a stable laminar flow with linear flow reductions of up to 2000. This means that an inlet tube diameter of 1/50 of the column diameter can be used.

Figure 4:
FIG. 4 is a sectional view of a further embodiment of the head according to the invention.

FIG. 4 shows a further embodiment of the head according to the invention.

In this embodiment the inlet tube 7 enters the head 8 tangentially at the perimeter of the head 8.

In order for the head 8 to uniformly disperse a liquid onto a bed (not shown) also in this embodiment, the vertical liquid flow through the bed should be equated to the horizontal liquid flow in the head 8. In this embodiment this means that liquid for the centre bed region must be supplied by liquid flowing from the perimeter of the head 8. In view hereof, the profile of the head be described by the equation $$h_x = \frac{x}{z},$$

where, as above, $h_x$ is the vertical distance between the base of the head 8 and the inside surface of the head at a distance x from the central vertical axis of the head, and z is a constant proportional to the back pressure of the column (not shown). In this embodiment x is smaller than or equal to the internal radius R of the column, and greater than or equal to 0.

Thus, the inside surface of the head 8 tapers linearly to the base of the head at the centre of the head.

Figure 3:
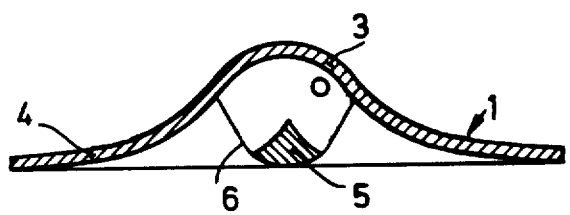
FIG. 3 is a sectional view of another embodiment of the head according to the invention.

As in the embodiments according to FIGS. 1-3, z would be equal to 2 if there was no back pressure to the liquid flow within the column (not shown), but since the liquid flow within the head 8 is, also, severely restricted by the relative high back pressure of the column, z is dependent on that back pressure as above.

I claim:

1. A head in a preparative column having a predetermined back pressure per unit flow rate for uniformly dispersing a liquid over the input surface of a chromatographic or reactive bed, comprising an inlet tube through which the liquid is supplied, a central domed part, into which the inlet tube enters, and which blends into a profiled lower part, said central domed part being adapted to form a laminar flow region of liquid prior to the liqud having an internal profile described by the equation $$h_x = \frac{1}{z}\left(\frac{R^2 - x^2}{x}\right),$$

where

R is the internal radius of the column, $h_x$ is the vertical distance between the base of the head and the inside surface of the profiled part at a distance x from the central vertical axis of the head, $R \geq x \geq R/15$, and z is a constant proportional to said back pressure.

2. A head according to claim 1, wherein the central domed part is either semi-spherical or of an arched vertical cross-sectional form.

3. A head according to claim 1, wherein the inlet tube is parallel to the base of the head and enters into the domed part at a point between a line through the central vertical axis of the head and a line tangential to the inside surface of the domed part.

4. A head according to claim 1, wherein $R \geq x \geq R/4$.

5. A head according to claim 1, wherein a distributing body is centrally supported in the space between the base of the head and the domed part.

6. A head in a preparative column having a predetermined back pressure per unit flow rate for uniformly dispersing a liquid over the input surface of a chromatographic or reactive bed, comprising an inlet tube through which the liquid is supplied, the inlet tube entering the head tangentially at its perimeter, and the internal profile of the head being described by the equation $$h_x = \frac{x}{z},$$

where $h_x$ is the vertical distance between the base of the head and the inside surface of the head at a distance x from the central vertical axis of the head, $R \geq x \geq 0$, R being the internal radius of the column and z is a constant proporional to said back pressure such that the internal surface of the head tapers linearly in a radial direction to the base of the head at the center of the head.

* * * * *

UNITED STATES PATENT AND TRADEMARK OFFICE
CERTIFICATE OF CORRECTION

PATENT NO. : 4,722,786

DATED : February 2, 1988

INVENTOR(S) : Victor C. Weaver

It is certified that error appears in the above-identified patent and that said Letters Patent is hereby corrected as shown below:

Column 4, line 1, after "the" should read -- liquid entering into the profiled lower part, said profiled lower part --.

Signed and Sealed this

Fifth Day of July, 1988

Attest:

DONALD J. QUIGG

Attesting Officer

Commissioner of Patents and Trademarks